United States Patent
Chin et al.

(10) Patent No.: US 10,406,533 B2
(45) Date of Patent: Sep. 10, 2019

(54) ELECTROMAGNETIC FLUID FILTER USING MAGNETOSTRICTIVE SENSORS

(71) Applicant: Auburn University, Auburn, AL (US)

(72) Inventors: Bryan A. Chin, Auburn, AL (US); Shin Horikawa, Auburn, AL (US); Steve R. Best, Montgomery, AL (US); I-Hsuan Chen, Auburn, AL (US); Zhongyang Cheng, Auburn, AL (US); Songtao Du, Auburn, AL (US)

(73) Assignee: Auburn University, Auburn, AL (US)

( * ) Notice: Subject to any disclaimer, the term of this patent is extended or adjusted under 35 U.S.C. 154(b) by 327 days.

(21) Appl. No.: 15/190,824

(22) Filed: Jun. 23, 2016

(65) Prior Publication Data

US 2017/0080436 A1    Mar. 23, 2017

Related U.S. Application Data

(60) Provisional application No. 62/184,052, filed on Jun. 24, 2015.

(51) Int. Cl.
*B03C 1/033* (2006.01)
*B03C 1/28* (2006.01)
(Continued)

(52) U.S. Cl.
CPC ............ *B03C 1/0335* (2013.01); *A23L 3/001* (2013.01); *A23L 3/26* (2013.01); *B01D 35/06* (2013.01);
(Continued)

(58) Field of Classification Search
CPC ..... B01D 35/06; B03C 1/034; B03C 2201/18; B03C 1/0335; B03C 1/035; B03C 1/12; B03C 1/284; B03C 1/286; B03C 2201/26; C02F 1/481; C02F 1/488; C02F 1/484; C02F 2103/32; A23L 3/001; A23L 3/26;
(Continued)

(56) References Cited

U.S. PATENT DOCUMENTS

| | | | | |
|---|---|---|---|---|
| 2,331,769 A | * | 10/1943 | Frantz | B03C 1/034 209/224 |
| 5,439,586 A | * | 8/1995 | Richards | A61M 1/3627 210/222 |

(Continued)

*Primary Examiner* — Claire A Norris
(74) *Attorney, Agent, or Firm* — Barnes & Thornburg LLP (57) ABSTRACT

In at least one illustrative embodiment, an electromagnetic filter may include a transfer pipe and multiple electromagnetic filter elements positioned in an interior volume of the pipe. Each electromagnetic filter element includes a support comb, a solenoid coupled to the support comb, and multiple magnetic members arranged in a planar array positioned within an opening of the support comb. Each magnetic member may rotate about an end that is coupled to the support comb. The magnetic members may be magnetostrictive sensors and may include a biorecognition element to bind with a target microorganism. A method for fluid filtration includes coupling the electromagnetic filter between a fluid source and a fluid destination, energizing the solenoids of each electromagnetic filter elements, and flowing a fluid media through the transfer pipe of the electromagnetic filter. The fluid media may be liquid food such as fruit juice. Other embodiments are described and claimed.

11 Claims, 4 Drawing Sheets

(51) Int. Cl.
*B01D 35/06* (2006.01)
*C02F 1/48* (2006.01)
*G01N 15/06* (2006.01)
*G01N 33/543* (2006.01)
*G01N 33/569* (2006.01)
*A23L 3/00* (2006.01)
*A23L 3/26* (2006.01)
*G01N 29/02* (2006.01)
*G01N 29/22* (2006.01)
*G01N 29/24* (2006.01)
*G01N 15/00* (2006.01)
*C02F 103/32* (2006.01)

(52) U.S. Cl.
CPC .............. *B03C 1/284* (2013.01); *B03C 1/286* (2013.01); *C02F 1/484* (2013.01); *G01N 15/0618* (2013.01); *G01N 15/0656* (2013.01); *G01N 29/022* (2013.01); *G01N 29/222* (2013.01); *G01N 29/24* (2013.01); *G01N 33/54373* (2013.01); *G01N 33/56911* (2013.01); *A23V 2002/00* (2013.01); *B03C 2201/18* (2013.01); *B03C 2201/26* (2013.01); *C02F 2103/32* (2013.01); *G01N 2015/0065* (2013.01); *G01N 2291/0256* (2013.01); *G01N 2291/0427* (2013.01)

(58) Field of Classification Search
CPC ............ A23V 2002/00; A61C 13/2656; A61C 2201/007; A61C 8/0057; A61C 8/0062; A61C 8/0065; G01N 15/0618; G01N 15/0656; G01N 2015/0065; G01N 2291/0256; G01N 2291/0427; G01N 29/022; G01N 29/222; G01N 29/24; G01N 33/54373; G01N 33/56911
USPC ........................ 210/695, 222, 223.1; 209/226
See application file for complete search history.

(56) References Cited

U.S. PATENT DOCUMENTS

| | | | |
|---|---|---|---|
| 6,896,801 B2 * | 5/2005 | Anderson | ................. B03C 1/20 209/213 |
| 2005/0074904 A1 * | 4/2005 | Chin | .................... G01N 27/745 436/526 |

* cited by examiner

ELECTROMAGNETIC FLUID FILTER USING MAGNETOSTRICTIVE SENSORS

CROSS-REFERENCE TO RELATED APPLICATION

This application claims priority to U.S. Provisional Application Ser. No. 62/184,052, filed Jun. 24, 2015, the entire disclosure of which is hereby incorporated by reference.

BACKGROUND

Foodborne illnesses are primarily caused by food contaminated with pathogenic microorganisms in the field or during food processing under unsanitary conditions. Hence, surveillance of bacterial contamination of fresh produce through the food supply chain is of great importance to the food industry. However, such surveillance is a challenge since the food supply chain is a lengthy trail with many opportunities to cause food contamination. Food products may be cleaned at the harvesting site, transported to a warehouse, re-cleaned, and repackaged several times before reaching retail outlets.

Typical microbiological methods for pathogen detection, such as colony counting, immunoassay, and polymerase chain reaction (PCR), offer very high sensitivities. However, they require pre-analytical sample preparation, which generally includes sample collecting, separating target pathogen cells from food, increasing cell concentration, and achieving analysis volume from bulk samples before detection. These processes are time consuming, resulting in delays in obtaining the screening results. Also, only small samples (for example, 1 mL samples) may be evaluated for pathogens. More importantly, food samples have to be delivered to laboratories for culture preparation and analysis. Label-free biosensors are available in today's market. However, they also require sample preparation prior to the actual testing (i.e. sampling from fresh produce, filtration and purification of the collected samples, and injection of the filtered/purified samples into a flow system where a biosensor resides). Due to the complexity of these test procedures and the requirements of expensive equipment and highly trained personnel, current food safety controls mainly rely on control of worker/environment hygiene in the food processing industry, rather than the direct pathogen detection.

Free-standing phage-based magnetoelastic biosensors have been investigated as a label-free wireless biosensor system for real-time pathogen detection. The magnetoelastic biosensor is typically composed of a magnetoelastic resonator that is coated with a bio-molecular recognition element that binds specifically with a target pathogen. Once the biosensor comes into contact with the target pathogen, binding occurs, causing an increase in the mass of the resonator resulting in a decrease in the resonant frequency of the sensor (as well as other characteristic frequencies of the sensor).

Fluids may be filtered for pathogens using a conventional bead filter. The bead filter may include many nanobeads, which may be coated with a bio-molecular recognition element that binds specifically with a target pathogen. To filter the fluid media, the nanobeads may be mixed throughout a relatively small sample (e.g., 1 gallon) of the fluid media, or the fluid media may be passed through a filter bed of nanobeads. However, the nanobeads may trap large debris that is not targeted by the biorecognition element, which may cause the filter to clog.

SUMMARY

According to one aspect, an electromagnetic filter element may include a support comb, a solenoid coupled to the support comb, and a plurality of elongated magnetic members. The support comb comprises a magnetic material and defines an opening. The solenoid is configured to, when energized, cause the support comb to generate a magnetic field. The plurality of magnetic members are arranged in a planar array positioned within the opening of the support comb. Each magnetic member comprises a first end and a second end, and the first end of each magnetic member is coupled to the support comb. In some embodiments, magnetization of the support comb may be controlled by the solenoid, each of the magnetic members may be magnetically coupled to the support comb, and each magnetic member may rotate about the first end of the magnetic member coupled to the support comb. In some embodiments, the first end of each magnetic member may be hingedly attached to the support comb.

In some embodiments, each magnetic member may comprise a magnetostrictive sensor comprising magnetostrictive material. Each magnetostrictive sensor may further comprise a biorecognition element to bind with a microorganism. The biorecognition element may comprise a bacteriophage that is genetically engineered to bind with the microorganism. In some embodiments, the support comb may comprise a high permeability magnetic material.

According to another aspect, an electromagnetic filter includes a transfer pipe that defines an interior volume and a plurality of electromagnetic filter elements positioned in the interior volume of the transfer pipe. Each of the electromagnetic filter elements comprises a support comb, a solenoid coupled to the support comb, and a plurality of elongated magnetic members. The support comb comprises a magnetic material and defines an opening. The opening describes a cross-section of the interior volume of the transfer pipe. The solenoid is configured to, when energized, cause the support comb to generate a magnetic field. The plurality of magnetic members are arranged in a planar array positioned within the opening of the support comb. Each magnetic member comprises a first end and a second end, and the first end of each magnetic member is coupled to the support comb. In some embodiments, each of the electromagnetic filter elements may have a different orientation of the plurality of magnetic members. In some embodiments, magnetization of each support comb may be controlled by the corresponding solenoid, each of the magnetic members may be magnetically coupled to the corresponding support comb, and each magnetic member may rotate about the first end of the magnetic member coupled to the corresponding support comb. In some embodiments, the first end of each magnetic member may be hingedly attached to the corresponding support comb.

In some embodiments, each magnetic member may comprise a magnetostrictive sensor comprising magnetostrictive material. Each magnetostrictive sensor may further comprise a biorecognition element to bind with a microorganism. The biorecognition element may comprise a bacteriophage that is genetically engineered to bind with the microorganism. In some embodiments, the support comb of each electromagnetic filter element may comprise a high permeability magnetic material.

According to another aspect, a method for fluid filtration comprises coupling a transfer pipe between a fluid source and a fluid destination, wherein the transfer pipe defines an interior volume and includes a plurality of electromagnetic filter elements positioned in the interior volume, wherein each of the electromagnetic filter elements comprises an electromagnet and a plurality of magnetic members positioned within the interior volume of the transfer pipe, wherein each magnetic member comprises a first end and a second end; energizing the electromagnet of each of the electromagnetic filter elements to cause the first end of each magnetic member to magnetically couple to the corresponding electromagnet of the electromagnetic filter element, wherein each magnetic member may rotate about the first end; and flowing a fluid media through the transfer pipe between the fluid source and the fluid destination in response to energizing the electromagnet of each of the electromagnetic filter elements. In some embodiments, the fluid media may comprise a liquid food product. In some embodiments, the fluid media may comprise process water, wash water, or irrigation water.

In some embodiments, each magnetic member may comprise a magnetostrictive sensor comprising magnetostrictive material. Each magnetostrictive sensor may further comprise a biorecognition element.

In some embodiments, the method may further include de-energizing the electromagnet of each of the electromagnetic filter elements in response to flowing the fluid media through the transfer pipe. In some embodiments, the method may further include collecting the magnetostrictive sensors in response to de-energizing the electromagnet of each of the electromagnetic filter elements and detecting microorganisms bound to the magnetostrictive sensors in response to collecting the magnetostrictive sensors.

In some embodiments, detecting the microorganisms may comprise applying a varying magnetic field, using a drive coil, to the magnetostrictive sensors; detecting a frequency response of the magnetostrictive sensors using a pickup coil, while applying the varying magnetic field; and determining whether a microorganism is present based on the detected frequency response of the magnetostrictive sensors. In some embodiments, detecting the microorganisms may further comprise positioning the pickup coil in proximity to the magnetostrictive sensors, wherein detecting the frequency response comprises detecting the frequency response in response to positioning the pickup coil. In some embodiments, detecting the microorganisms may include culturing the microorganisms bound to the magnetostrictive sensors.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the present disclosure.

References in the specification to "one embodiment," "an embodiment," "an example embodiment," etcetera, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Figure 1:
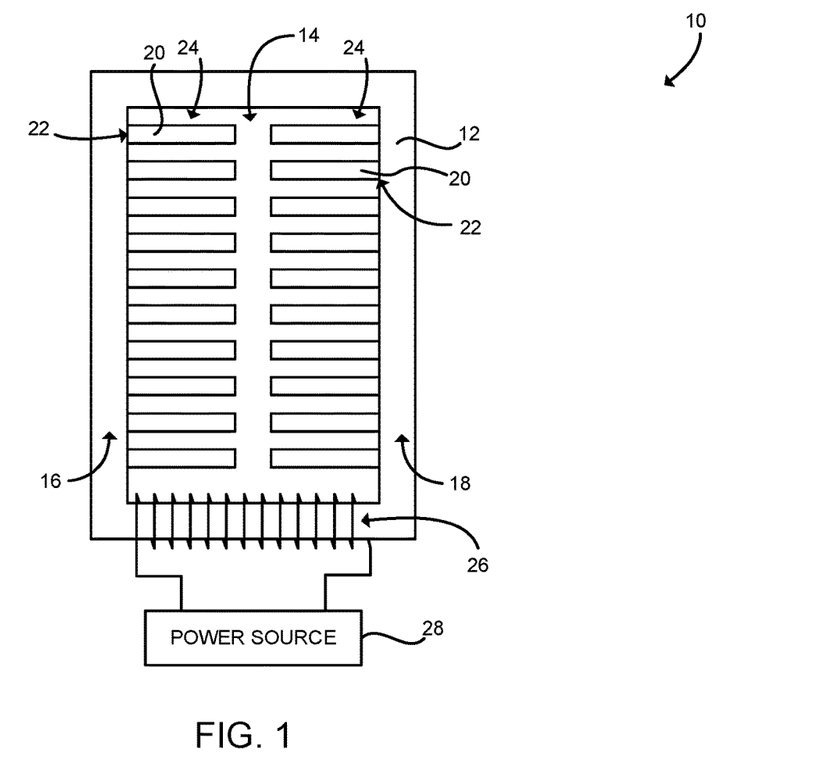
FIG. 1 is a simplified schematic diagram of an electromagnetic filter element using magnetostrictive members.

Referring now to FIG. 1, a simplified schematic diagram of one illustrative embodiment of an electromagnetic filter element 10 is shown. The electromagnetic filter element 10 includes a support comb 12 and multiple magnetic members 20 coupled to the support comb 12. In use, as described further below, a solenoid 26 of the electromagnetic filter element 10 may be energized to create a magnetic field. A fluid flows through the electromagnetic filter element 10 and targeted contaminants such as pathogens bind to the magnetic members 20. Large, non-binding debris may pass through the electromagnetic filter element 10, pushing the magnetic members 20 out of the way. After the debris passes, the magnetic field generated by the electromagnetic filter element 10 forces the magnetic members 20 back to their original position. Thus, and as described further below, the electromagnetic filter element 10 may be used to filter and detect small concentrations of contaminants (such as pathogens) in large volumes of fluid. Thus, rather than analyzing small (e.g., 1 mL) samples of fluid, the electromagnetic filter element 10 may be used to detect the presence of pathogens in an entire volume of fluid. Additionally, the electromagnetic filter element 10 may be resistant to clogging in the presence of large debris.

As shown in FIG. 1, the electromagnetic filter element 10 includes the support comb 12, which may be embodied as any magnetic material whose magnetization may be controlled by the solenoid 26. For example, the support comb 12 may be made of a material with high permeability, such as silicon steel. The support comb 12 defines an interior opening 14 surrounded by two sides 16, 18. The support comb 12 and the interior opening 14 are illustratively a planar rectangular in shape; however, in other embodiments the support comb 12 may have any shape that defines an interior opening 14.

As shown, the electromagnetic filter element 10 includes multiple magnetic members 20 positioned in an array in the interior opening 14. In the illustrative embodiment, each of the magnetic members 20 is a magnetostrictive sensor. The magnetostrictive sensors 20 are small devices made of a magnetostrictive and/or magnetoelastic material coated with a biorecognition element that binds to a particular target particle, such as a pathogen. For example, the biorecognition element may include antibodies or genetically engineered phages that bind to particular bacteria, such as *Salmonella typhimurium*. The magnetostrictive material converts magnetic energy to mechanical energy and vice versa. In other words, magnetostrictive materials generate mechanical strain when the magnetic energy is applied and generate magnetic energy in response to mechanical strain. Throughout this disclosure, the terms magnetostrictive material and magnetoelastic material may be used interchangeably. In the illustrative embodiment, the magnetostrictive sensors 20 are embodied as thin strips of material that may be actuated into resonance by application of a varying magnetic field. The magnetostrictive sensors 20 are illustratively rectangular in shape; however, in other embodiments, any elongated shape may be used. Upon contact with the specific target pathogen, the pathogen binds with the biorecognition element and increases the mass of the magnetostrictive sensor 20. This additional mass causes the characteristic frequency of the magnetostrictive sensors 20 to decrease. As described further below, the characteristic frequency may be measured by a pickup coil, allowing quantitative detection and characterization of the pathogen. One embodiment of a magnetostrictive sensor 20 is further described below in connection with FIG. 2.

As shown, each of the magnetic members 20 has an elongated shape with one end coupled to one of the sides 16, 18 the support comb 12 at a pivot point 22. As shown, the magnetic members 20 are illustratively arranged in two ranks 24 within a planar array. The members 20 of each rank 24 are coupled to a respective side 16, 18 of the support comb 12. The members 20 extend away from their respective side 16, 18 to cover the interior opening 14 of the support comb 12. Each magnetic member 20 may rotate about the pivot point 22, allowing large debris to pass through the interior opening 14 of the support comb 12. As described further below, each magnetic member 20 may be coupled to the support comb 12 by a magnetic force. Additionally or alternatively, in some embodiments each magnetic member 20 may be mechanically attached to the support comb 12, for example with a hinge. Additionally, although illustrated as including a single interior opening 14 with two ranks 24 of magnetic members 20, it should be understood that in some embodiments the support comb 12 may have multiple interior openings 14 and/or additional ranks 24 of magnetic members 20.

The illustrative electromagnetic filter element 10 further includes a solenoid 26 coupled to the support comb 12. The solenoid 26 is connected to a power source 28, which is configured to supply electrical current to the solenoid 26. When energized by the power source 28, the solenoid 26 and the support comb 12 together function as an electromagnet, generating a magnetic field. The magnetic field attracts the magnetic members 20 to the support comb 12, coupling each magnetic member 20 to the support comb 12 at the pivot point 22. As described further below, the magnetic field may be strong enough to couple the magnetic members 20 to the support comb 12 but also allow the magnetic members 20 to rotate about the pivot point 22 to allow large, non-binding debris to pass through the interior opening 14 of the support comb 12. After the debris passes, the magnetic field causes the magnetic members 20 to re-align across the interior opening 14. The strength of the magnetic field (and therefore the strength of the magnetic force acting on the magnetic members 20) may be adjusted by controlling the voltage and/or current supplied to the solenoid 26 or, in some embodiments, adjusting the number of windings and/or gauge of wire used to form the electromagnet. In some embodiments, the position that the magnetic members 20 attach to the support comb 12 may be controlled by coating the support comb 12 with a magnetic insulation layer using microelectronics fabrication techniques. The support comb 12 may be uncoated at the pivot points 22, caused the magnetic members 20 to be attracted to the support comb 12 at the pivot points 22.

Figure 2:
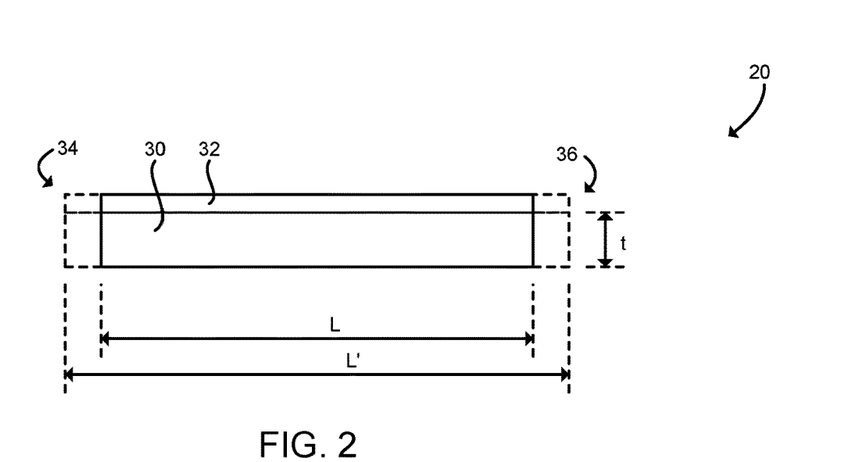
FIG. 2 is a simplified cross-sectional diagram of a magnetostrictive sensor of the electromagnetic filter element of FIG. 1.

Referring now to FIG. 2, a simplified schematic diagram of one illustrative embodiment of a magnetostrictive sensor 20 of the electromagnetic filter element 10 is shown. The sensor 20 includes a body 30 coated with an immobilized biorecognition element 32. The body 30 is made from a magnetoelastic material, such as a magnetostrictive alloy. In one illustrative embodiment, the body 30 may be mechanically polished and cut (diced) from a strip of METGLAS™ 2826MB, which is commercially available from Honeywell Inc., of Conway, S.C. As shown, the body 30 has two ends 34, 36. As shown in FIG. 1, one of the ends 34, 36 may be attached to a side 16, 18 of the support comb 12 at the pivot point 22, and the other end 34, 36 extends away from the side 16, 18 to cover the interior opening 14 of the support comb 12. Additionally, although illustrated as including a single side of the body 30 coated with the biorecognition element 32, it should be understood that in some embodiments two or more sides of the body 30 may be coated with the biorecognition element 32.

In the illustrative embodiment, each magnetostrictive sensor 20 has a length L, a thickness t, and a width w (not shown). For example, in some embodiments the magnetostrictive sensors 20 may be one millimeter in length, four millimeters in length, or another length. The magnetostrictive sensor 20 is in the shape of a thin strip, meaning that the length L is larger than the width w and much larger than the thickness t (i.e., L>w>>t). Upon application of a varying magnetic field, the dimensions of the magnetostrictive sensor 20 change. Accordingly, the magnetostrictive sensor 20 mechanically vibrates in response to the varying magnetic field. In particular, due to its thin strip shape, the magnetostrictive sensor 20 vibrates mainly longitudinally; in other words, when an oscillating external magnetic field is applied, the magnetostrictive sensor 20 vibrates between the length L and a length L'. The fundamental resonant frequency of this longitudinal oscillation is given as:

$$f_0 = \frac{V}{2L}, \quad (1)$$

where V is the acoustic velocity of the material along its length L. Addition of a small mass ($\Delta m \ll M$) on the magnetostrictive sensor 20 surface causes a change in the resonant frequency ($\Delta f$). This resonant frequency change is proportional to the initial frequency $f_0$ and the mass added ($\Delta m$) and is inversely proportional to the initial sensor mass M. Assuming the added mass is uniformly distributed on the surface of the magnetostrictive sensor 20, the resonant frequency change may be approximated as:

$$\Delta f = -\frac{f_0 \Delta m}{2M} \quad (\Delta m \ll M). \tag{2}$$

The negative sign in Equation (2) means that the resonant frequency of the magnetostrictive sensor 20 decreases with the increase of the mass load. The additional mass load on the magnetostrictive sensor 20 can be obtained by measuring the shift in the resonant frequency (or another characteristic frequency related to the resonant frequency).

When the magnetostrictive sensor 20 comes into contact with a target pathogen, the biorecognition element 32 immobilized on the magnetostrictive sensor 20 surface will bind/capture the target pathogen. This adds an additional mass load on the magnetostrictive sensor 20. As described above, this additional mass causes a drop in a characteristic frequency of the magnetostrictive sensor 20. Therefore, the presence of any target pathogens can be identified by monitoring for a shift in the characteristic frequency of the magnetostrictive sensor 20. Additionally or alternatively, rather than a biorecognition element 32, the magnetostrictive sensor 20 may include a chemical layer that similarly binds with one or more contaminants such as mercury or heavy metals.

The simple strip-shaped configuration of the illustrative magnetostrictive sensor 20 described above may make fabrication relatively easy and/or inexpensive. Additionally, the magnetostrictive sensors 20 are passive sensors that do not require on-board power. As described above, the magnetostrictive sensor 20 may be fabricated by mechanical methods (e.g., polish and dice) or by microelectronics fabrication methods (e.g., sputter deposit, thermal deposit, or electrochemical deposit). These methods can mass-produce fabricated magnetostrictive sensors 20 with very low cost. Additional details of illustrative magnetoelastic ligand detectors are described in U.S. Pat. No. 7,759,134 ("Magnetostrictive Ligand Sensor"), the entire disclosure of which is incorporated herein by reference.

As described above, the biorecognition element 32 may be immobilized on the surface of each magnetostrictive sensor 20 to bind a specific target pathogen. In some embodiments, the biorecognition element 32 may be embodied as a chemical binding element or an interaction layer immobilized on the body 30 of the magnetostrictive sensor 20. For example, the biorecognition element 32 may be a traditional antibody. Additionally or alternatively, in some embodiments, the biorecognition element 32 may be a genetically engineered bacteriophage ("phage"). The use of phages as a substitute for antibodies offers a stable, reproducible, and inexpensive alternative. In particular, phages have high affinity for binding with target pathogen cells, the phage structure is robust and stable, and phages may bind target pathogens in air with certain humidity. Additionally or alternatively, the biorecognition element 32 may be embodied as DNA, RNA, proteins, aptamers, or other biorecognition elements. Specific ligand recognition devices that may be illustratively used as the biorecognition element 32, as well as illustrative application methods, are discussed in U.S. Pat. No. 7,138,238 ("Ligand Sensor Devices and Uses Thereof"), U.S. Pat. No. 7,267,993 ("Phage Ligand Sensor Devices and Uses Thereof"), and U.S. Pat. No. 7,670,765 ("Method of Forming Monolayers of Phage-Derived Products and Used Thereof"), the entire disclosures of which are incorporated herein by reference.

Figure 3:
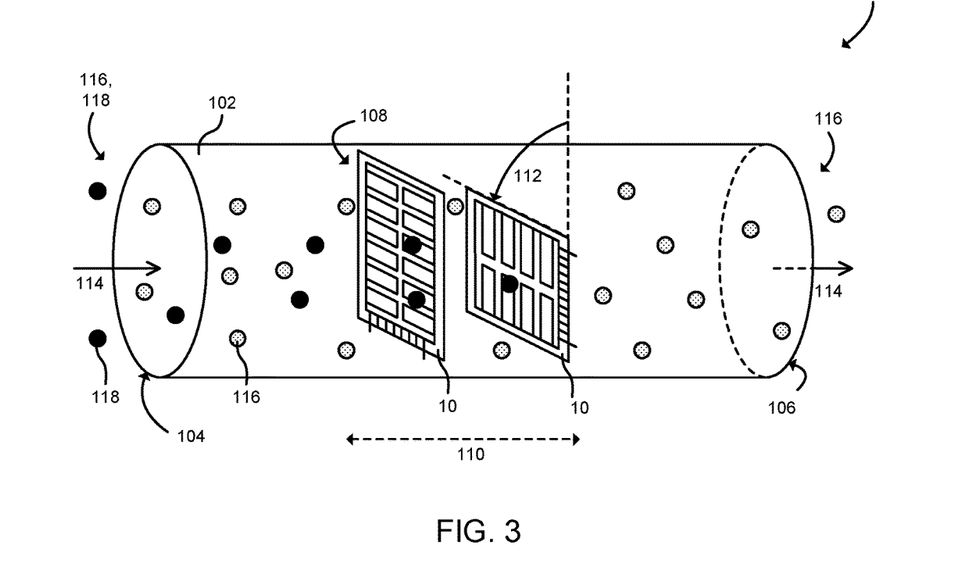
FIG. 3 is a simplified schematic diagram of an electromagnetic filter including multiple electromagnetic filter elements of FIGS. 1 and 2.

Referring now to FIG. 3, a simplified schematic diagram of one illustrative embodiment of an electromagnetic filter 100 is shown. The electromagnetic filter 100 includes a transfer pipe 102 having two ends, an inlet 104 and an outlet 106. The transfer pipe 102 may be embodied as any nonmagnetic material capable of transferring large volumes of fluid, such as PVC, plastic, or nonmagnetic metallic material, or as any other material that does not generate an excessively strong magnetic field. In use, as described further below, the transfer pipe 102 may be connected between a fluid source and a fluid destination, for example between two fluid tanks. Although illustrated as having a circular cross-section, it should be understood that in other embodiments the transfer pipe 102 be a square tube, spiral tube, or any other shaped tube capable of carrying fluid.

The electromagnetic filter 100 includes, within the transfer pipe 102, a filter assembly 108. The filter assembly 108 includes one or more electromagnetic filter elements 10. The electromagnetic filter elements 10 may be positioned at different linear positions 110 within the nonmetallic transfer pipe 102, essentially "stacking" the electromagnetic filter elements 10 within the nonmetallic transfer pipe 102. Each of the electromagnetic filter elements 10 may be fixed or otherwise attached within the nonmetallic transfer pipe 102 at a different orientation 112. For example, the support combs 12 of each electromagnetic filter element 10 may be positioned at different relative angles from each other, causing the magnetic members 20 to also be positioned at different relative angles. In some embodiments, by being positioned at different orientations 112, the stack of electromagnetic filter elements 10 may completely cover a cross-section of the nonmetallic transfer pipe 102 with the magnetic members 20. Each of the electromagnetic filter elements 10 may be removable from the filter assembly 108. Although the illustrative electromagnetic filter 100 includes two electromagnetic filter elements 10, it should be understood that in some embodiments the electromagnetic filter 100 may include many more electromagnetic filter elements 10.

In use, as described further below, a fluid media 114 may flow through the transfer pipe 102 and the filter assembly 108. The fluid media 114 may be embodied as any fluid that may include pathogens or other contaminant particles. For example, the fluid media 114 may be embodied as a liquid food product (e.g., milk or juice), process water, wash water (e.g., from washing fresh produce), irrigation water, blood or bodily fluids, oil, air, or other fluids. As shown, the fluid media 114 entering the inlet 104 of the transfer pipe 102 may include multiple non-binding particles 116 and binding particles 118. The binding particles 118 may be embodied as any contaminant particle to be trapped and removed from the fluid media 114 by the electromagnetic filter 100, such as a microorganism (e.g., bacteria, viruses, spores, mold, or other microorganisms, including pathogens), metallic particles, magnetic particles, chemicals, or any other particle or other contaminant that binds to the magnetic members 20 of the electromagnetic filter elements 10. The non-binding particles 116 may be embodied as any other particle or debris included in the fluid media 114, such as a non-binding food component. As the fluid media 114 flows through the filter assembly 108, the binding particles 118 bind to the magnetic members 20 in the filter assembly 108 and are thereby removed from the fluid media 114. The fluid media 114 leaving the outlet 106 of the transfer pipe 102 may include only non-binding particles 116 without including any binding particles 118 (or including a reduced concentration of binding particles 118).

Figure 4A:
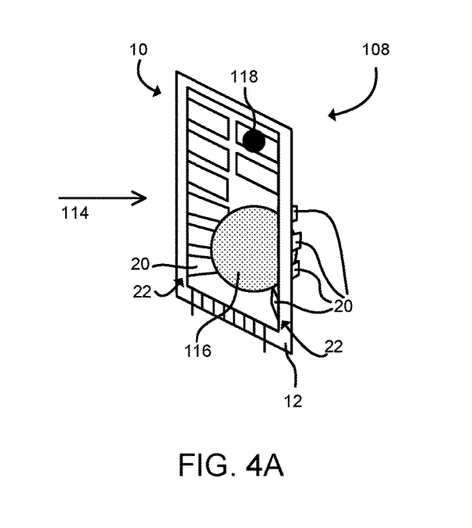
FIGS. 4A and 4B are simplified schematic diagrams illustrating large debris passing through an electromagnetic filter element of FIGS. 1-3.

Referring now to FIG. 4A, a simplified schematic diagram of an electromagnetic filter element 10 filtering fluid media 114 including a large non-binding particle 116 is shown. As shown, the non-binding particle 116, for example a large piece of debris, passes through the internal opening 14 of the electromagnetic filter element 10, and the magnetic members 20 are pushed by the non-binding particle 116 out of the way. Each magnetic member 20 may pivot, bend, flex, shift, or otherwise move about the pivot point 22, allowing the non-binding particle 116 to pass through the electromagnetic filter element 10. Because the non-binding particle 116 is not magnetic and does not bind to any biorecognition element of the magnetic members 20, the non-binding particle 116 is not bound or otherwise trapped by the magnetic members 20.

Figure 4B:
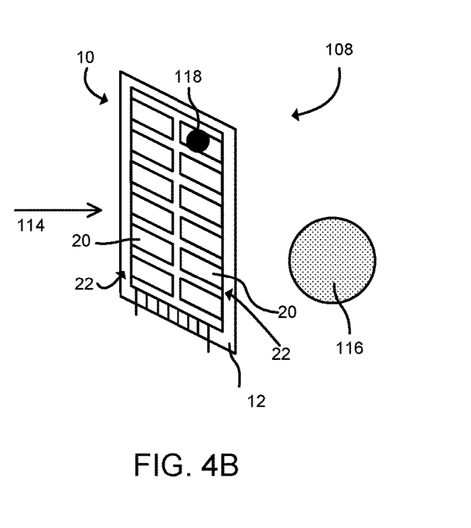

Referring now to FIG. 4B, a simplified schematic diagram of the electromagnetic filter element 10 after filtering the fluid media 114 including the large non-binding particle 116 is shown. As shown, the magnetic members 20 have returned to their original positions in the internal opening 14 of the electromagnetic filter element 10. For example, the magnetic field generated by the solenoid 26 may force the magnetic members 20 back to their original positions. Thus, the non-binding particle 116 may pass through the electromagnetic filter element 10 without obstructing the electromagnetic filter element 10, and the electromagnetic filter element 10 may continue to filter out binding particles 118.

Figure 5:
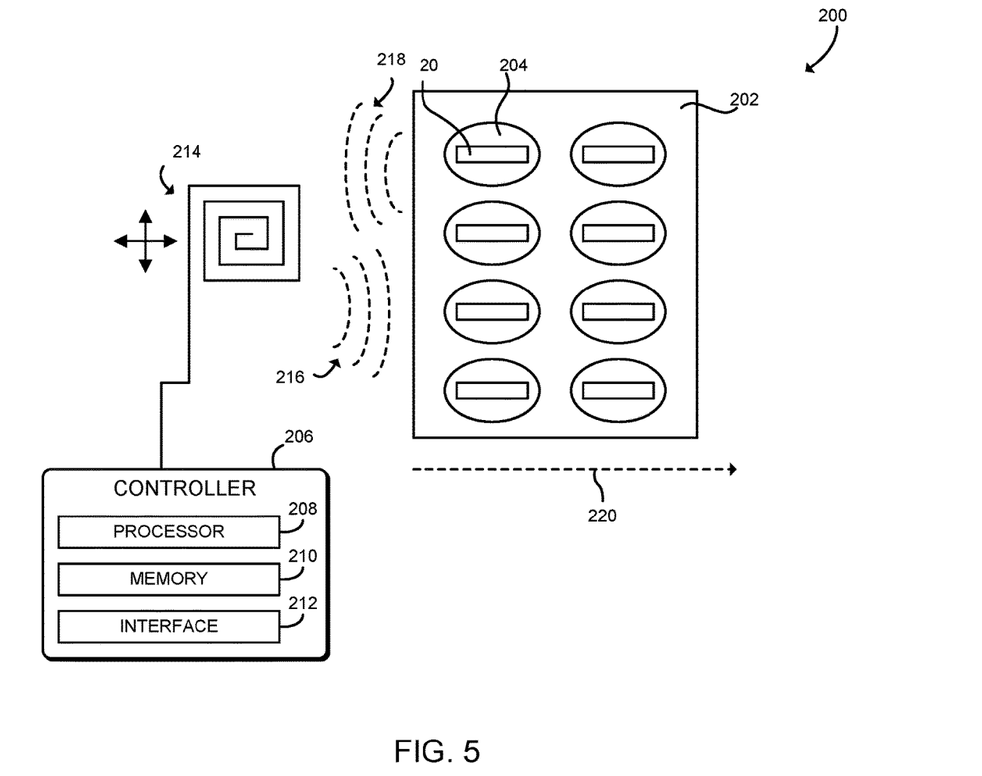
FIG. 5 is a simplified schematic diagram of a system for detecting pathogens captured by an electromagnetic filter element of FIGS. 1-4A and 4B.

Referring now to FIG. 5, a system 200 for detecting pathogens trapped by an electromagnetic filter element 10 is shown. The system 200 includes an indexing plate 202 that includes multiple analysis wells 204. The indexing plate 202 may be embodied as, for example, a silicon wafer that includes the analysis wells 204. The indexing plate 202 may be moveable, for example with a three-axis translation stage, to allow precise positioning of the analysis wells 204. Each of the analysis wells 204 may be filled with a fluid such as water or a cell growth medium. As shown, each of the analysis wells 204 may contain one or more magnetic members 20 from an electromagnetic filter element 10. In the illustrative embodiment, the magnetic members 20 are magnetostrictive sensors coated with a biorecognition element that binds with a particular pathogenic microorganism. As described further below in connection with FIG. 7, when the solenoid 26 of the electromagnetic filter element 10 is de-energized, the magnetic members 20 may be released from the support comb 12 and may be transferred or otherwise collected in the analysis wells 204.

The system 200 also includes a controller 206 coupled to a surface-scanning detector 214. The surface-scanning detector 214 may be positioned over one or more of the analysis wells 204 of the indexing plate 202. The surface-scanning detector 214 and/or the indexing plate 202 may be movable to position the detector 214 over a particular analysis well 204. The surface-scanning detector 214 may further include a drive coil and a pickup coil. The controller 206 causes the drive coil to apply a varying magnetic field 216 to the magnetostrictive sensors 20. The controller 206 measures a magnetic field 218 produced by the magnetostrictive sensors 20 in response to the varying magnetic field 216 using the pickup coil. The controller 206 determines a characteristic frequency of the magnetostrictive sensors 20 based on the measured magnetic field 218. This characteristic frequency is related to the resonant frequency of the magnetostrictive sensors 20, as well as other material properties (e.g., the magnetoelastic coupling coefficient) and the environment (e.g., friction forces or damping effects). As described further below, binding particles 118 present in the fluid media 114 flowed through the electromagnetic filter element 10 may bind with the magnetostrictive sensors 20, causing an increase in the mass of the magnetostrictive sensors 20 and a corresponding decrease in the characteristic frequency. The system 200 may determine whether the binding particles 118 (e.g., a pathogen or other contaminant) are present by determining whether the characteristic frequency shifts. Multiple types of binding particles 118, for example, multiple types of pathogens, may be detected simultaneously by using separate groups of magnetostrictive sensors 20, with each group of magnetostrictive sensors 20 binding to a different type of binding particle 118. Additionally, although described as including both a drive coil and a pickup coil, it should be understood that in some embodiments the surface-scanning detector 214 may include a single test coil to generate the varying magnetic field 216 and measure the magnetic field 218 produced by the magnetostrictive sensors 20. In some embodiments, the surface-scanning detector 214 may include an array of pickup coils and/or test coils to measure the magnetic field 218 produced by magnetostrictive sensors 20 in several analysis wells 204 simultaneously.

As described briefly above, the system 200 includes the controller 206. The controller 206 is responsible for activating or energizing electronically-controlled components of the system 200, including the drive coil of the surface-scanning detector 214. The controller 206 is also responsible for interpreting electrical signals received from other components of the system 200, including the pickup coil. To do so, the controller 206 may include a number of electronic components commonly associated with units utilized in the control of electronic and electromechanical systems. For example, the controller 206 may include, amongst other components customarily included in such devices, a processor 208 and a memory device 210. The processor 208 may be any type of device capable of executing software or firmware, such as a microcontroller, microprocessor, digital signal processor, or the like. The memory device 210 may be embodied as one or more non-transitory, machine-readable media. The memory device 210 is provided to store, amongst other things, instructions in the form of, for example, a software routine (or routines) which, when executed by the processor 208, allows the controller 206 to perform pathogen detection using the other components of the system 200.

The controller 206 also includes an analog interface circuit 212, which may be embodied as any electrical circuit(s), component, or collection of components capable of performing the functions described herein. The analog interface circuit 212 converts output signals (e.g., from the pickup coil) into signals which are suitable for presentation to an input of the processor 208. In particular, the analog interface circuit 212, by use of a network analyzer, an analog-to-digital (A/D) converter, or the like, converts analog signals into digital signals for use by the processor 208. Similarly, the analog interface circuit 212 converts signals from the processor 208 into output signals which are suitable for presentation to the electrically-controlled components associated with system 200 (e.g., the drive coil). In particular, the analog interface circuit 212, by use of a variable-frequency signal generator, digital-to-analog (D/A) converter, or the like, converts digital signals generated by the processor 208 into analog signals for use by the electronically-controlled components associated with the system 200.

It is contemplated that, in some embodiments, the analog interface circuit 212 (or portions thereof) may be integrated into the processor 208.

As also mentioned above, the surface-scanning detector 214 includes a drive coil and one or more pickup coil(s). In the illustrative embodiment, the drive coil is used as an energizing excitation source for the magnetostrictive sensors 20 and the pickup coil is used as a detector of signals received from the magnetostrictive sensors 20. In some embodiments, the drive coil and/or the pickup coil may be a solenoid with loops having a generally rectangular cross-section. To improve performance of the system 200, the drive coil and/or the pickup coil may be impedance-matched to the electrical circuitry of the controller 206. In some embodiments, the surface-scanning detector 214 may include a test coil that performs the functions of both a drive coil and a pickup coil.

The system 200 may further include a magnetic field generator configured to generate a constant, uniform magnetic field 220. The uniform magnetic field 220 extends through the analysis wells 204. The uniform magnetic field 220 may align the magnetostrictive sensors 20, which may improve the sensitivity, signal-to-noise ratio, or other operating characteristics of the magnetostrictive sensors 20 and thereby improve accuracy of the system 200. The uniform magnetic field 220 may also bias the magnetostrictive sensors 20 during application of the varying magnetic field 216, increasing the magnitude of the response signal 218. The magnetic field generator may be embodied as any component capable of generating the uniform magnetic field 220, for example, a pair of permanent magnet arrays or a Helmholtz coil.

Figure 6:
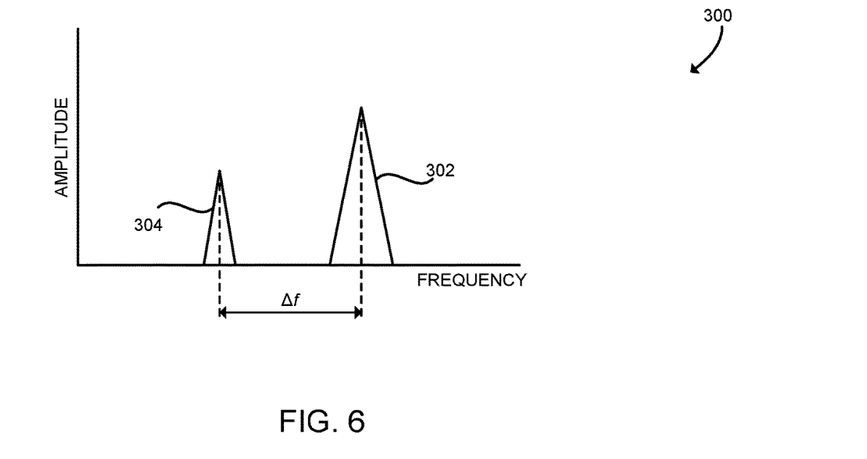
FIG. 6 is an exemplary plot of magnetostrictive sensor frequency response that may be measured using the system of FIG. 5.

Referring now to FIG. 6, an exemplary plot 300 illustrates results that may be measured when binding particles 118 are detected. Plot 300 illustrates signal amplitude against frequency f. Curves 302, 304 illustrate the frequency response for the magnetostrictive sensors 20. Curve 302 illustrates the frequency response for the magnetostrictive sensors 20 when not bound to any binding particle 118, including a strong peak at the unloaded characteristic frequency. Curve 304 illustrates the frequency response of the magnetostrictive sensors 20 when bound to the binding particle 118, including a smaller peak shifted from the unloaded characteristic frequency to a lower frequency by an amount $\Delta f$. These results may indicate that some of the magnetostrictive sensors 20 have bound with the binding particle 118 and experienced a frequency shift.

Figure 7:
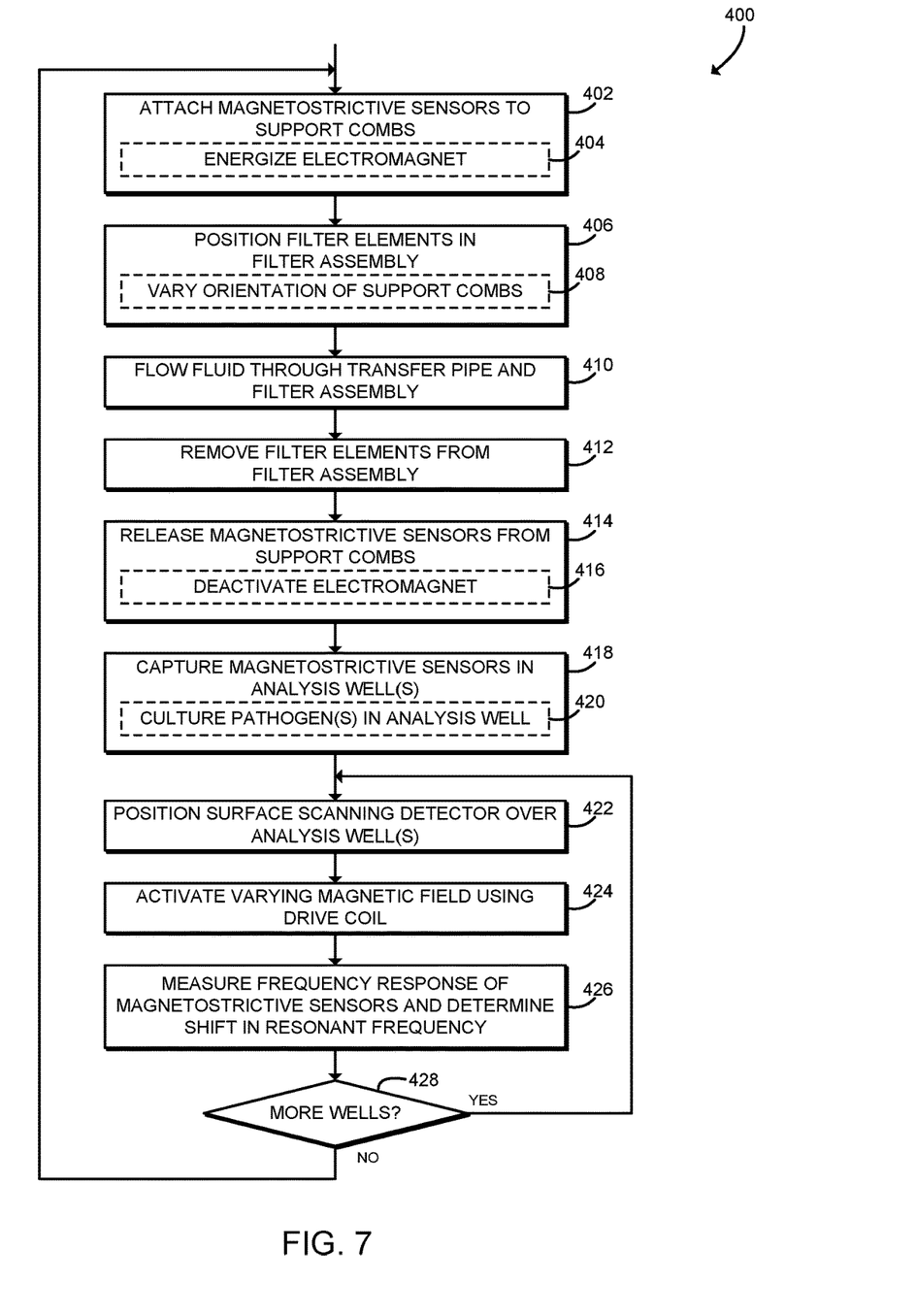
FIG. 7 is a simplified flow diagram of one embodiment of a method for fluid filtering and pathogen detection that may be performed using the electromagnetic filter element, electromagnetic filter, and system of FIGS. 1-6.

Referring now to FIG. 7, one illustrative embodiment of a method 400 that may be used for fluid filtration and pathogen detection with the electromagnetic filter 100 and the measurement system 200 is shown as a simplified flow diagram. The method 400 is illustrated as a series of blocks 402-428, some of which may be optionally performed in some embodiments (and, thus, are shown in dashed lines). It will be appreciated by those of skill in the art that some embodiments of the method 400 may include additional or different processes and sub-processes.

The method 400 begins with block 402, in which magnetostrictive sensors 20 are attached to the support comb 12 of one or more electromagnetic filter elements 10. As described above, the magnetostrictive sensors 20 may be magnetically or mechanically attached to the support comb 12, and each magnetostrictive sensor 20 can rotate about the pivot point 22. In some embodiments, in block 404, an electromagnet of the electromagnetic filter element 10 may be energized to attach the magnetostrictive sensors 20 to the support comb 12. For example, the magnetostrictive sensors 20 may be arranged in a planar array on a surface such as the indexing plate 202. The support comb 12 may be moved in proximity to the magnetostrictive sensors 20, and the solenoid 26 may then be energized in order to magnetically attach the magnetostrictive sensors 20 to the support comb 12. After being energized, the support comb 12 may be lifted from the surface, also lifting the magnetically attached magnetostrictive sensors 20.

In block 406, the electromagnetic filter elements 10, including the magnetostrictive sensors 20, are positioned in the filter assembly 108. For example, the electromagnetic filter elements 10 may be inserted into the filter assembly 108, which may include, for example, one or more rails, slots, or other mounting points to receive the electromagnetic filter elements 10. As shown in FIG. 3, the filter assembly 108 may be positioned within the transfer pipe 102. For example, the filter assembly 108 may also be inserted or otherwise positioned in the transfer pipe 102, or the filter assembly 108 may be fixed within the transfer pipe 102. By positioning the electromagnetic filter elements 10 in the transfer pipe 102, the magnetostrictive sensors 20 are positioned within the interior volume of the transfer pipe 102. In some embodiments, in block 408 the orientation 112 of the support combs 12 of each electromagnetic filter element 10 may be varied. Varying the orientation 112 may improve coverage by the magnetostrictive sensors 20 of the cross-section of the transfer pipe 102.

In block 410, the fluid media 114 flows through the transfer pipe 102 and the filter assembly 108. As described above, the fluid media 114 may be embodied as any fluid that may include binding particles 118 such as pathogens or other contaminant particles. For example, the fluid media 114 may be embodied as a liquid food product, process water, wash water, irrigation water, blood or bodily fluids, oil, air, or other fluids. The inlet 104 of the transfer pipe 102 may be coupled to a fluid source and the outlet 106 may be coupled to a fluid destination (as well as any intermediate piping). For example, the inlet 104 of the transfer pipe 102 may be coupled to a large tanker truck full (e.g., 1500 gallons) of liquid food such as apple juice or milk, and the outlet 106 of the transfer pipe 102 may be coupled to a similarly-sized destination tank. As another example, the inlet 104 of the transfer pipe 102 may receive wash water created by washing a large amount of produce (e.g., produce from an entire field or other harvest). As the fluid media 114 flows through the filter assembly 108 and the electromagnetic filter elements 10, any binding particles 118 in the fluid media 114 may bind with the magnetostrictive sensors 20 and become trapped within the filter assembly 108. As illustrated in FIGS. 4A and 4B, any large non-binding particles 116 (e.g., debris) in the fluid media 114 may cause the magnetostrictive sensors 20 to rotate about the pivot point 22 and allow the large debris to pass through the filter assembly 108. Binding particles 118 may remain bound to the magnetostrictive sensors 20 even in the presence of large debris. Thus, a large amount of fluid media 114, potentially including debris or other solid material (e.g., non-binding food components), may pass through the filter assembly 108 without clogging. The fluid media 114 may flow through the transfer pipe 102 and the filter assembly 108 until a large sample of the fluid media 114 has been filtered or until the fluid source has completely emptied into the fluid destination.

In the illustrative embodiment, the magnetostrictive sensors 20 trap one or more binding particles 118 that are bound by the biorecognition element of the magnetostrictive sensors 20. However, it should be understood that in some embodiments the magnetostrictive sensors 20 may bind to any targeted organism, chemical contaminants, metallic or magnetic particles, or other contaminant particles. In some embodiments, some of the magnetostrictive sensors 20 may include different biorecognition elements to target different binding particles 118 (e.g., targeting multiple pathogens). Additionally, in some embodiments, the magnetic members 20 may bind to metallic particles or other magnetic particles in the fluid media 114 using magnetic effects, rather than a biorecognition element.

In block 412, the electromagnetic filter elements 10 are removed from the filter assembly 108. The magnetostrictive sensors 20 remain attached to the support comb 12 of each electromagnetic filter element 10; therefore, any binding particles 118 bound to the magnetostrictive sensors 20 are also removed from the filter assembly 108. Additionally or alternatively, it should be understood that in some embodiments the entire filter assembly 108 may be removed from the transfer pipe 102, the transfer pipe 102 may be disconnected from the fluid source and/or destination, or any other technique may be used to remove the electromagnetic filter elements 10.

In block 414, the magnetostrictive sensors 20 are released from the support combs 12 of the electromagnetic filter elements 10. Prior to being released, the support combs 12 may be positioned appropriately to facilitate collecting the magnetostrictive sensors 20. In some embodiments, in block 416, the electromagnet of the electromagnetic filter element 10 may be de-energized or otherwise deactivated. For example, the solenoid 26 may be de-energized, releasing the magnetostrictive sensors 20 from the support comb 12.

In block 418, the magnetostrictive sensors 20 are captured in the analysis wells 204 of the indexing plate 202. For example, the support comb 12 may be positioned over the indexing plate 202 prior to releasing the magnetostrictive sensors 20. After the solenoid 26 is de-energized, the magnetostrictive sensors 20 may drop into the analysis wells 204. In some embodiments, in block 420, pathogens in the analysis wells 204 may be cultured. For example, the analysis wells 204 may include a cell growth medium and the indexing plate 202 may be stored, incubated, or otherwise given time to allow any pathogens in the analysis wells 204 to multiply.

In block 422, the surface-scanning detector 214 is positioned over the analysis wells 204. For example, the surface-scanning detector 214 may move and/or a three-axis translation stage may position the indexing plate 202 such that one or more of the analysis wells 204 are positioned in proximity to the surface-scanning detector 214. The controller 206 may move the surface-scanning detector 214 over the analysis wells 204 in a pre-defined pattern such as a raster scan pattern. Additionally or alternatively, in some embodiments an array of pickup coils may be positioned over multiple analysis wells 204 for simultaneous measurement.

In block 424, the drive coil of the surface-scanning detector 214 is activated to generate the varying magnetic field 216. As described above, the varying magnetic field 216 causes the magnetostrictive sensors 20 to oscillate. The frequency of the varying magnetic field 216 may be varied through a range of frequencies. The range of frequencies may include a characteristic frequency of the magnetostrictive sensors 20 when the binding particle 118 has not been bound (i.e., when the sensors 20 are unloaded). For example, in some embodiments the range of frequencies applied by the drive coil may cover from 50% of unloaded characteristic frequency to slightly more than the unloaded characteristic frequency. Binding of binding particles 118 on the magnetostrictive sensor 20 surface is typically a small mass change, and the decrease in the characteristic frequency of the magnetostrictive sensors 20 due to this small mass change is normally less than 50% of the unloaded characteristic frequency of the magnetostrictive sensor 20. Decreases in characteristic frequency beyond that range are unlikely to be due to binding of binding particles 118. In some embodiments, the uniform magnetic field 220 may also be applied to the magnetostrictive sensors 20. As described above, the uniform magnetic field 220 may bias the sensors 20 and increase the magnitude of the response signal 218. Additionally, the uniform magnetic field 220 may align the sensors 20 in the direction of the uniform magnetic field 220. This alignment of the sensors 20 causes the longitudinal oscillation of all (or, at least, most) of the sensors 20 to be in the same direction. In this way, the pickup coil may not need to align with individual sensors 20. The magnetic flux picked up by the pickup coil may thus contain frequency response information for all (or, at least, most) of the sensors 20. Additionally or alternatively, the uniform magnetic field 220 may polarize the magnetoelastic material of the sensors 20, resulting in amplified and quasi-linear response.

In block 426, the frequency response of the magnetostrictive sensors 20 is measured using the pickup coil, and any shift in resonant frequency of the magnetostrictive sensors 20 is determined. The controller 206 may monitor the characteristic frequency in real time or record data for later analysis. As described above, the magnetostrictive sensors 20 include the biorecognition element 32 that will bind with binding particles 118 upon contact. Binding with the binding particles 118 increases the mass of the magnetostrictive sensor 20, which causes a characteristic frequency of the magnetostrictive sensor 20 to decrease. Thus, a measured shift in the resonant frequency indicates that the binding particles 118 were filtered out of the fluid media 114. In some embodiments, the detection of the binding particles 118 may be repeated over time. For example, when culturing any pathogens in the analysis wells 204, the resonant frequency of the magnetostrictive sensors 20 may be measured over time. A change in the resonant frequency may indicate that the pathogens filtered from the fluid media 114 are reproducing and therefore are live. The change in resonant frequency may also be measured to indicate the concentration of the measured pathogen in the original fluid media 114.

In block 428, it is determined whether additional analysis wells 204 should be measured. For example, the controller 206 may determine whether additional analysis wells 204 remain in a pre-programmed pattern of analysis wells 204. As another example, additional analysis wells 204 may be measured after some elapsed time, such as when culturing pathogens in the analysis wells 204. Of course, as described above, in some embodiments all of the analysis wells 204 may be measured simultaneously, for example using an array of pickup coils. If additional analysis wells 204 should be measured, the method 400 loops back to block 422, in which the surface-scanning detector 214 may be positioned over additional analysis wells 204. If no further analysis wells 204 remain to be measured, the method 400 may loop back to block 402 to re-load the electromagnetic filter elements 10 and perform additional filtration.

Although FIG. 7 illustrates the operations of the method 400 as being performed in linear order, it should be understood that in some embodiments those operations may be performed in a different order and/or some of those operations may not be performed. For example, in some embodiments, the fluid media 114 may be filtered with the electromagnetic filter 100 as described in connection with blocks 402-410 without detecting the presence of the binding particles 118 or with detecting the presence of the binding particles 118 at a later time. As another example, an electromagnetic filter 100 may be assembled and loaded with magnetic members 20 as described above in connection with blocks 402-408 and then used to filter fluids at a later time.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present disclosure.

The invention claimed is:

1. An electromagnetic filter element comprising:
a support comb comprising a magnetic material, wherein the support comb defines an opening;
a solenoid coupled to the support comb and configured to, when energized, cause the support comb to generate a magnetic field; and
a plurality of elongated magnetic members arranged in a planar array positioned within the opening of the support comb, wherein each magnetic member comprises a first end and a second end, and wherein the first end of each magnetic member is coupled to the support comb at a corresponding pivot point, wherein each magnetic member is rotatable about the corresponding pivot point.

2. The electromagnetic filter element of claim 1, wherein magnetization of the support comb is controlled by the solenoid, wherein each of the magnetic members is magnetically coupled to the support comb, and wherein each magnetic member may rotate about the first end of the magnetic member coupled to the support comb.

3. The electromagnetic filter element of claim 1, wherein the first end of each magnetic member is hingedly attached to the support comb.

4. The electromagnetic filter element of claim 1, wherein each magnetic member comprises a magnetostrictive sensor comprising magnetostrictive material.

5. The electromagnetic filter element of claim 4, wherein each magnetostrictive sensor further comprises a biorecognition element to bind with a microorganism.

6. The electromagnetic filter element of claim 5, wherein the biorecognition element comprises a bacteriophage that is genetically engineered to bind with the microorganism.

7. An electromagnetic filter comprising:
a transfer pipe that defines an interior volume; and
a plurality of electromagnetic filter elements positioned in the interior volume of the transfer pipe, wherein each of the electromagnetic filter elements comprises:
a support comb comprising a magnetic material, wherein the support comb defines an opening, wherein the opening describes a cross-section of the interior volume of the transfer pipe;
a solenoid coupled to the support comb and configured to, when energized, cause the support comb to generate a magnetic field; and
a plurality of elongated magnetic members arranged in a planar array positioned within the opening of the support comb, wherein each magnetic member comprises a first end and a second end, and wherein the first end of each magnetic member is coupled to the support comb at a corresponding pivot point, wherein each magnetic member is rotatable about the corresponding pivot point.

8. The electromagnetic filter of claim 7, wherein each of the electromagnetic filter elements has a different orientation of the plurality of magnetic members.

9. The electromagnetic filter of claim 7, wherein magnetization of each support comb is controlled by the corresponding solenoid, wherein each of the magnetic members is magnetically coupled to the corresponding support comb, and wherein each magnetic member may rotate about the first end of the magnetic member coupled to the corresponding support comb.

10. The electromagnetic filter of claim 7, wherein each magnetic member comprises a magnetostrictive sensor comprising magnetostrictive material.

11. The electromagnetic filter of claim 10, wherein each magnetostrictive sensor further comprises a biorecognition element to bind with a microorganism.

\* \* \* \* \*